United States Patent
Rahmel et al.

(10) Patent No.: US 10,252,014 B2
(45) Date of Patent: Apr. 9, 2019

(54) DEVICE AND SYSTEM FOR DELIVERY OF AN AEROSOL TO A PATIENT ON VENTILATORY SUPPORT

(75) Inventors: Daniela Rahmel, Hamburg (DE); Friedemann Taut, Konstanz (DE); Christian De Muynck, Konstanz (DE); Peter Iwatschenko, Eckenthal (DE); Wolfgang Koch, Steimbke (DE); Gerhard Pohlmann, Meerbeck (DE); Horst Windt, Burgwedel (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 261 days.

(21) Appl. No.: 13/813,669

(22) PCT Filed: Aug. 8, 2011

(86) PCT No.: PCT/EP2011/063645
§ 371 (c)(1),
(2), (4) Date: Feb. 13, 2013

(87) PCT Pub. No.: WO2012/020004
PCT Pub. Date: Feb. 16, 2012

(65) Prior Publication Data
US 2013/0152925 A1 Jun. 20, 2013

(30) Foreign Application Priority Data
Aug. 9, 2010 (EP) .................................. 10172317

(51) Int. Cl.
*A61M 11/00* (2006.01)
*A61M 16/06* (2006.01)
*A61M 16/14* (2006.01)
*A61M 16/12* (2006.01)
*A61M 16/10* (2006.01)
*A61M 16/16* (2006.01)

(52) U.S. Cl.
CPC .... *A61M 16/0666* (2013.01); *A61M 16/1065* (2014.02); *A61M 16/12* (2013.01);
(Continued)

(58) Field of Classification Search
CPC .............. A61M 11/00; A61M 16/0666; A61M 16/0683; A61M 16/1065; A61M 16/12;
(Continued)

(56) References Cited

U.S. PATENT DOCUMENTS 3,473,530 A * 10/1969 Urbanowicz .......... A61M 11/06
222/199
5,186,166 A * 2/1993 Riggs .................... A61M 15/00
128/203.15

(Continued)

FOREIGN PATENT DOCUMENTS

EP  2 075 023 A1  7/2009
WO  2005/102431 A2  11/2005

(Continued)

Primary Examiner — Peter S Vasat
(74) Attorney, Agent, or Firm — Nath, Goldberg & Meyer; Joshua B. Goldberg; Tanya E. Harkins

(57) ABSTRACT

A device and system for delivering an aerosol to a patient on ventilatory support comprise a contact component 10 to be positioned in contact with a respiratory organ. The contact component 10 comprises a lumen 18a, 20a, 24 through which breathing gas and an aerosol are delivered to lungs of a patient.

13 Claims, 5 Drawing Sheets

(52) U.S. Cl.
CPC ............ *A61M 16/14* (2013.01); *A61M 11/00* (2013.01); *A61M 16/0683* (2013.01); *A61M 16/16* (2013.01); *A61M 2202/0208* (2013.01); *A61M 2240/00* (2013.01)

(58) Field of Classification Search
CPC ................. A61M 16/14; A61M 16/16; A61M 2202/0208; A61M 2240/00; A61M 15/08; A61M 16/0677
USPC ........... 128/200.14, 200.15, 200.16, 200.17, 128/200.18, 200.19, 200.21, 200.22, 128/200.23, 203.15, 203.16, 204.12, 128/206.11, 207.18
See application file for complete search history.

(56) References Cited

U.S. PATENT DOCUMENTS

| | | | |
|---|---|---|---|
| 5,724,965 A * | 3/1998 | Handke | A61M 16/06 128/205.25 |
| 5,975,077 A | 11/1999 | Hofstetter et al. | |
| 7,047,968 B2 | 5/2006 | Kniewasser | |
| 7,195,018 B1 * | 3/2007 | Goldstein | A61M 16/0683 128/200.24 |
| 2003/0200970 A1 | 10/2003 | Stenzler et al. | |
| 2004/0020488 A1 * | 2/2004 | Kniewasser | A61M 11/00 128/204.18 |
| 2005/0217666 A1 * | 10/2005 | Fink | A61K 31/7036 128/200.14 |
| 2006/0120968 A1 | 6/2006 | Niven et al. | |
| 2009/0173350 A1 | 7/2009 | Swanson | |
| 2011/0108025 A1 * | 5/2011 | Fink | A61M 11/005 128/200.16 |

FOREIGN PATENT DOCUMENTS

| | | |
|---|---|---|
| WO | 2006/108558 A1 | 10/2006 |
| WO | 2007/064660 A2 | 6/2007 |
| WO | 2007/064668 A2 | 6/2007 |
| WO | 2009/078805 A1 | 6/2009 |
| WO | 2009/117422 A2 | 9/2009 |

* cited by examiner

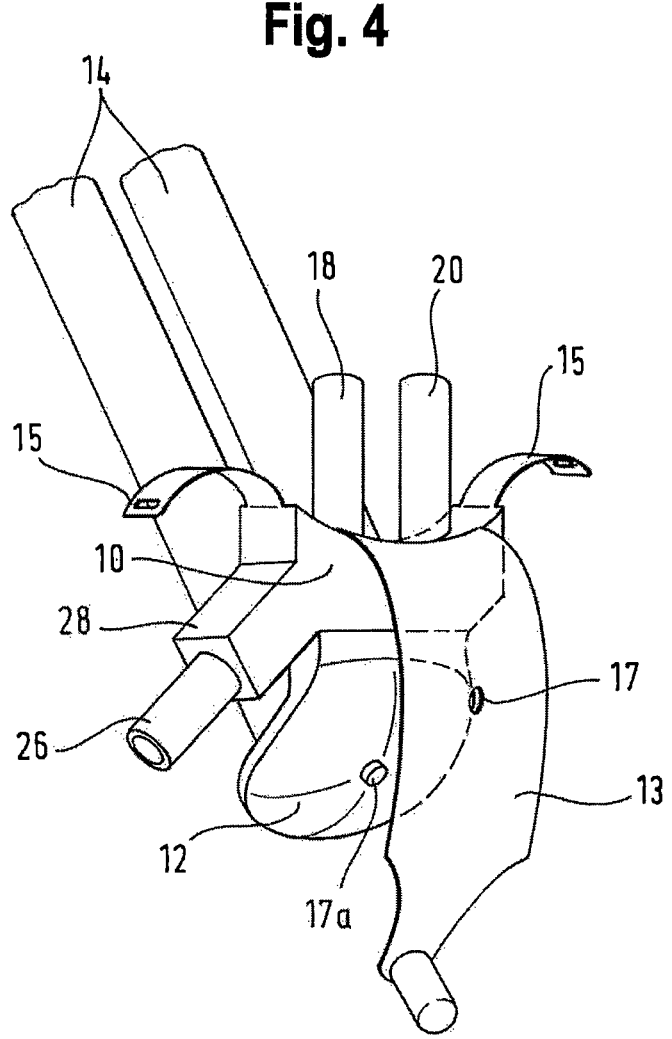

DEVICE AND SYSTEM FOR DELIVERY OF AN AEROSOL TO A PATIENT ON VENTILATORY SUPPORT

This is a National Phase Application filed under 35 U.S.C. 371 as a national stage of PCT/EP2011/063645, filed Aug. 8, 2011, and claims priority from European Application No. 10172317.9, filed Aug. 9, 2010, the content of each of which is hereby incorporated by reference in its entirety.

The present invention relates to a device for connection with the airways of a patient on ventilatory support, and a system for ventilating a patient using such a device. The ventilatory support can be provided by complex ventilators or by simple devices or systems for generating pressure support such as CPAP (Continuous Positive Airway Pressure) systems, or by any other means of providing breathing support to a patient in need thereof. As used herein, the term "ventilatory support" is also meant to comprise the administration to a patient of air enriched in oxygen (i.e., having a partial pressure of $O_2$ above the level of atmospheric air), even if no positive pressure is applied.

Patients (including adults, children, infants, neonates and pre-term neonates) suffering from respiratory dysfunction or being at risk thereof are nowadays preferably treated with non-invasive ventilatory support (e.g., CPAP or non-invasive positive pressure ventilation, NIPPV), as long as intubation and mechanical ventilation can be avoided.

An example of a system for providing ventilatory support to a patient including an adaptor for delivering an aerosolized active agent is disclosed in WO 2009/117422 A2. This adaptor can be used for mixing a breathing gas and the aerosol agent. Said adaptor, however, is not positioned in contact with an opening to the atmosphere of the patient's airways (i.e., the nose or the mouth of the patient). Rather, this prior art utilizes a patient interface, such as an endotracheal tube, a mask, or nasal prongs, to which said adaptor is connected. The known system uses a well-known CPAP technique for ventilatory support. The present invention also, preferably, utilizes CPAP for providing ventilatory support to a patient, but can also be used with alternative modes of noninvasive ventilatory support, e.g., NIPPV. A comparable system is disclosed in US 2006/0120968, which, too, relates to an adaptor for delivering an aerosolized active agent to a patient, wherein the active agent may be pulmonary surfactant ("lung surfactant"). This invention is concerned with the problem that, when an aerosol is mixed with the breathing air of a ventilated patient in a way known from the art, deposits are formed which should not be delivered to the patient. The problem is solved by providing a fluid flow connector capable of collecting deposits associated with the aerosolized active agent outside the main aerosol flow path.

US 2009/0173350 is concerned with a nasal cannula having a hollow body and a pair of nasal prongs useful for simultaneously measuring a patient's respiratory pressure and monitoring the composition of exhaled gases. Aerosol delivery to the patient is not disclosed. U.S. Pat. No. 7,047,968 B2 discloses a CPAP device allowing to introduce a flow of medicament into a hollow body under overpressure which is also connected to a source of breathing air such that a vortex effect is caused. Outwardly pointing pipe stubs which serve for introduction into a nosepiece or mouthpiece are oriented such that their longitudinal axes are parallel to the longitudinal axis of the hollow body. The flow of medicament is, due to the vortex effect, vigorously mixed with the CPAP air flowing through the hollow body, leading to substantial losses of unused medicament leaving the hollow body through an opening instead of being inhaled by the patient. Further, due to the intended vortex effect, formation of depositions is a disadvantage of this device as soon as the introduced medicament is an aerosol.

WO 2009/078805 teaches a nebulizing device usable for adding, in a CPAP system, a nebulized drug to the flow of air to be inhaled by the patient, wherein the angle at which the stream of nebulized drug enters the flow of air to be inhaled is at least 120° and, in certain embodiments, up to 180°. As mentioned in the context of U.S. Pat. No. 7,047,968 B2, the disclosed geometry of the nebulizing device according to WO 2009/078805 causes undesired losses of nebulized drug due to the formation of depositions, either in the device or in the upper airways of the patient, or both.

Accordingly, the technical problem underlying the present invention is to provide a device and a system with enhanced efficiency for aerosol application to the lung of the patient, and in particular a device and a system which avoid or significantly reduce the formation of depositions when administering an aerosol to a patient on ventilator support.

In this regard, the present invention provides a device for connection of the airways of a patient on ventilatory support with a source of breathing gas and a source of an aerosol, said device comprising a contact component to be positioned in contact with the patient's airways and comprising a lumen through which breathing gas and aerosol can be delivered to the airways, wherein said contact component comprises a port through which aerosol can be introduced into said lumen.

The aerosol delivered in connection with the present invention, along with the breathing gas (containing either a normal (21%) or an elevated fraction of oxygen), may contain (and preferably does contain) lung surfactant. In a particularly preferred embodiment, the lung surfactant comprises rSP-C or derivatives thereof such as, e.g., rSP-C-FF/I (a recombinant truncated mutant derivative peptide of human SP-C having three point mutations). However, any other pharmaceutical composition that can be aerosolized (either as dry powder or as a solution or suspension) can be used with the present invention as well. Examples comprise compositions containing antibiotic or anti-neoplastic drugs, enzymes (e.g., DNAse), siRNAs etc.

In a preferred embodiment, the contact component comprises one or two tubes protruding from the body of the contact component which can be inserted into the patient's airways, e.g. into one or both nostrils, into the nasal cavity, or the pharynx or other parts of the airways, or, via the mouth, to the pharynx or other parts of the airways. Each of the one or two tubes comprises a first lumen through which breathing gas and aerosol can be delivered to the airways of the patient.

The contact component also comprises a mixing lumen (the "second lumen", the terms "mixing lumen" and "second lumen" being interchangeably used herein) which is in fluid connection with the lumens of the one or two tubes (the "first lumens") and having a longitudinal axis extending substantially perpendicularly to longitudinal axes of the tube's or tubes' lumen(s). The mixing lumen ("second lumen") could also be called "stratification lumen" since the mixing, as can also be understood from the figures, is accomplished in a way that preferably the aerosol is delivered to the patient during inhalation and only secondarily the breathing gas. "Substantially perpendicularly", as used herein, means 90°, 90°±0.5°, 90°±1°, 90°±2°, 90°±3°, 90°±4°, 90°±5°, 90°±7°, 90°±10° or 90°±15°. Further meanings of "substantially perpendicularly" include the ranges of 90° to 90.5°, 90° to 91°, 90° to 92°, 90° to 93°, 90° to 94°, 90° to 95°, 90° to 97°, 90° to 100° or 90° to 105°.

Further, said mixing lumen (the "second lumen") may be in fluid connection with a port which port being configured to allow the aerosol to be introduced into the mixing lumen such that the aerosol and a breathing gas can be mixed in the mixing lumen. The port could be configured to direct the aerosol into said mixing lumen coaxially or at an acute angle with respect to a longitudinal axis of the lumen. According to the present invention, the port is configured to introduce the aerosol essentially perpendicularly to the longitudinal axis of one of the tubes into said lumen.

In a preferred embodiment the contact component is a nasal prong or a set of nasal prongs, and the tubes disposed on the contact component may be inserted into the respiratory system, in particular into one or both nostrils. One of said tubes may be longer than the other of said tubes.

It has to be noted that the term "nasal prong" is not used consistently in the literature. While in a narrow sense a nasal prong is a tube to be inserted into a nostril, this term frequently is used for what also could be described as a "set of nasal prongs", i.e., two tubes which usually are (but don't necessarily need to be) substantially parallel to each other, which protrude from a body having at least one lumen and which are in fluid connection with said at least one lumen (the body further having an inlet for breathing gas connectable to a source of breathing gas, the inlet being in fluid connection with said at least one lumen). In the context of this specification the latter definition is used, i.e. a "nasal prong" as used herein means a pair of tubes called nasal tubes (although embodiments having a single nasal tube are also part of the invention) insertable into a patient's airways, the tubes protruding from a body having a lumen and an inlet for breathing gas, the lumens of the tubes, the body and the inlet being in fluid connection.

Accordingly, in one embodiment, the present invention relates to a device for connection of the airways of a patient on ventilatory support with a source of a breathing gas and a source of an aerosol, said device comprising a contact component (10) adapted to be positioned in contact with the airways, the contact component (10) comprising:
  one or two tubes (18, 20) each comprising a first lumen (18a, 20a) through which breathing gas and aerosol can be delivered to the airways of the patient;
  a second lumen (the "mixing lumen") (24) which is in fluid connection with the first lumen or lumens (18a, 20a) of the tube or the two tubes (18, 20) and having a longitudinal axis (24c) extending substantially perpendicularly to longitudinal axis or axes (18c, 20c) of the first lumen or lumens (18a, 20a); and
  a port (28) through which aerosol can be introduced into said second lumen (24) and arranged such that the aerosol and a breathing gas can be mixed in the second lumen (24),
the device being characterized by a third lumen (12a) being connected to a device for generating a flow of breathing gas, wherein the second lumen (24) is positioned proximal to, and is in fluid connection with, said third lumen (12a).

In a preferred embodiment, the third lumen (12a) is connected to the device for generating a flow of breathing gas via two tubes. In a further preferred embodiment, the connection of the third lumen (12a) to the device for generating a flow of breathing gas is positioned at the third lumen's distal end.

The contact component may be adapted to be removably connected to a contact component holder. In this embodiment, it is preferred that the third lumen (12a) is positioned in the contact component holder. The contact component may comprise an inlet lumen adapted to receive a contact component holder lumen, such that the inlet lumen is in fluid connection with the mixing lumen.

The component holder is adapted to hold the contact component such that the lumens of the contact component and the contact component holder, respectively, are in fluid connection.

The system for providing ventilatory support to a patient in accordance with the present invention comprises
  the above-mentioned device for connection with the patient's airways,
  a device for generating a flow of breathing gas (a "source of breathing gas"),
  optionally a holder for holding a contact component of said device for connection with the patient's airways, and
  means for generating an aerosol,
  wherein
  flows of breathing gas and aerosol are introduced into said contact component.

In embodiments comprising a contact component holder, the holder and the contact component may be detachably connectable. The holder comprises a lumen in fluid connection with the lumen of the contact component.

The contact component may comprise a flexible strap which is detachably connectable at said holder or any other means which allows to securely attach the contact component to the holder.

The device and system according to the present invention preferably use the CPAP (Continuous Positive Airway Pressure) technology mentioned above. A particularly favourable application of the device and system according to the present invention is the administration of lung surfactant to patients suffering from a deficit of lung surfactant and sequelae thereof. A particularly important application is the administration of lung surfactant to preterm neonates.

As is outlined above, the present invention is characterized by providing a contact component adapted to be positioned in physical contact with the airways of the patient, e.g. with the nose (or, more precisely, with the nostrils), wherein the contact component itself comprises a port through which aerosol can be introduced into a lumen within the contact component.

In terms of the above-cited prior art, the contact component of the present invention can be called a patient interface. A nasal prong is a typical contact component according to the invention, wherein the nasal prong (contact component) comprises one or two tubes adapted to be inserted into the nostrils, and wherein said tube or tubes is/are integrally formed with a contact component body. Said body may comprise a lumen within which the breathing gas, containing oxygen, and the aerosol are mixed.

In the context of this specification, the terms "proximal" and "distal" are defined from the perspective of the patient, i.e. "proximal" means close to the patient and "distal" means more remote from the patient.

The present invention teaches to introduce the aerosol into said mixing lumen in the contact component positioned directly distally from said two tubes of the nasal prong, wherein said two tubes of the nasal prong are in direct fluid communication with said lumen. Of course, while this specification refers to nasal prongs comprising two tubes, embodiments having only a single tube to be inserted into the patient's airways are encompassed as well.

Said contact component, if implemented in the form of a nasal prong including one or two tubes to be inserted into the nostrils, may be made integrally as one piece.

Also, preferably, the contact component is made from silicone.

The device and system according to the present invention are non-invasive.

The device and system according to the present invention allow an essentially loss-free administration of aerosol into the lungs of the patient. The formation of depositions by precipitation of aerosol particles from the gas phase within the device or the system is minimized. The same holds true for the formation of depositions within the patient's upper airways. The aerosol is completely, or at least substantially, mixed with the breathing gas that is actually inhaled by the patient.

According to a preferred embodiment of the invention, if implemented in form of a nasal prong having two tubes, one of the tubes of the prong may be longer than the other tube.

Typically, according to the prior art, said tubes of the nasal prong have a circular cross-section. According to one aspect of the present invention, said tubes have a non-circular cross-section and the outer contour of the tubes is adapted to the internal shape of the body opening into which the tube is to be inserted, e.g. the nostril.

While the tubes of a nasal prong having two tubes usually are parallel to each other, it is also possible to position them in a way that their axes are forming an angle.

According to another preferred embodiment, the contact component of the device is adapted to be removably connected to a holder for holding the contact component. Said holder then usually comprises the third lumen (12a) that is connected to a device for generating a flow of breathing gas, which device can be a ventilator, a CPAP machine or the like. The connection of the third lumen (12a) to the device for generating a flow of breathing gas can be at the third lumen's distal end. The connection of the third lumen (12a) to the device for generating a flow of breathing gas can be accomplished via two tubes. At the proximal end thereof, the third lumen (12a) in the holder is in fluid connection with the second lumen, which usually is positioned in the contact component. The latter connection is preferably achieved through a detachable plug-like connector that is inserted so as to closely fit into an opening provided in said contact component.

Accordingly, in a further embodiment, the present invention relates to a device for connection of the airways of a patient on ventilatory support with a source of a breathing gas and a source of an aerosol, said device comprising a contact component (10) adapted to be positioned in contact with the airways and being adapted to be removably connected to a contact component holder (12), the contact component (10) comprising:
  one or two tubes (18, 20) each comprising a first lumen (18a, 20a) through which breathing gas and aerosol can be delivered to the airways of the patient;
  a second lumen (the "mixing lumen") (24) which is in fluid connection with the first lumen or lumens (18a, 20a) of the tube or the two tubes (18, 20) and having a longitudinal axis (24c) extending substantially perpendicularly to longitudinal axis or axes (18c, 20c) of the first lumen or lumens (18a, 20a); and
  a port (28) through which aerosol can be introduced into said mixing lumen (24) and arranged such that the aerosol and a breathing gas can be mixed in the mixing lumen (24), characterized in that the contact component holder (12) comprises a third lumen (12a) being connected to a device for generating a flow of breathing gas, wherein the second lumen (24) is positioned proximal to, and is in fluid connection with, said third lumen (12a).

In a further embodiment, both the second and third lumens are positioned in the contact component holder.

The present invention is based on the finding that efficiency of a loss-free delivery of aerosol into a patient's lungs depends on the direction of aerosol flow relative to the axes of the above-mentioned tube or tubes of the nasal prong (if the invention is implemented in connection with such a prong or a comparable device). A lumen in the body of the contact component, into which the aerosol is injected, connects both tubes of the nasal prong (or is connected to the one tube, if the prong is equipped with only one tube). Said tubes of the prong each have a longitudinal axis extending, in use, into the nasal opening. The aerosol is injected into the lumen in a certain direction, which may be called the "aerosol flow direction". The aerosol flow direction can be arranged relative to the direction of a longitudinal axis of the nasal prong tubes (or the longitudinal axes, if the tubes are not parallel to each other). Furthermore, the aerosol flow direction can be described in relation to the longitudinal axis of said lumen within the contact component. Said lumen extends, as is outlined above, between the longitudinal axes of the prong tubes. In other words, said longitudinal axis of the lumen is perpendicular or essentially perpendicular to the longitudinal axes of the prong tubes (or to the angle bisector of the longitudinal axes, if the tubes are not parallel to each other).

According to the present invention, the aerosol flow direction is arranged laterally or at an acute angle with regard to the longitudinal axis of a tube of the prong.

If the flow direction of the aerosol with regard to the contact component is described in connection with the above-defined longitudinal axis of the lumen in the contact component, the aerosol flow direction may be essentially in the same direction as the longitudinal axis of the lumen in the contact component. This embodiment can be said to have "tangential" flow. It has been found that the efficiency of the aerosol delivery to the lungs depends on the above-discussed aerosol flow direction. Experimental in vivo studies with lambs have shown that coaxial arrangement of the aerosol flow direction and the prong tube longitudinal axis (or an arrangement close to such a coaxial arrangement) results in extremely high efficiency with respect to aerosol delivery to the lungs but shows an undesirable and, in a clinical setting, dangerous tendency of deposition formation of particles precipitating from the aerosol in the upper airways of the respiratory system, which is possibly caused by higher velocities in the respective tube. In particular in case of airways having very small diameters, such as in the case of newborn infants or even preterm neonates, the formation of depositions needs to be reduced as far as possible or even completely avoided due to the danger of clog formation, which, in extreme cases, might lead to suffocation. The inventors have now found that, having an aerosol flow direction in a lateral direction, i.e. substantially perpendicular to said longitudinal axes of the prong tubes ("tangential flow"), while resulting in a somewhat lower efficiency regarding aerosol delivery to the lungs, allows to reduce turbulence, which results in a significantly smaller tendency of deposition formation of aerosol in the upper airways of the respiratory system.

Further preferred embodiments of the present invention are described in dependent claims.

FIG. 4 shows a detached perspective view of a device according to one of the FIG. 1 or 2;

Figure 1:
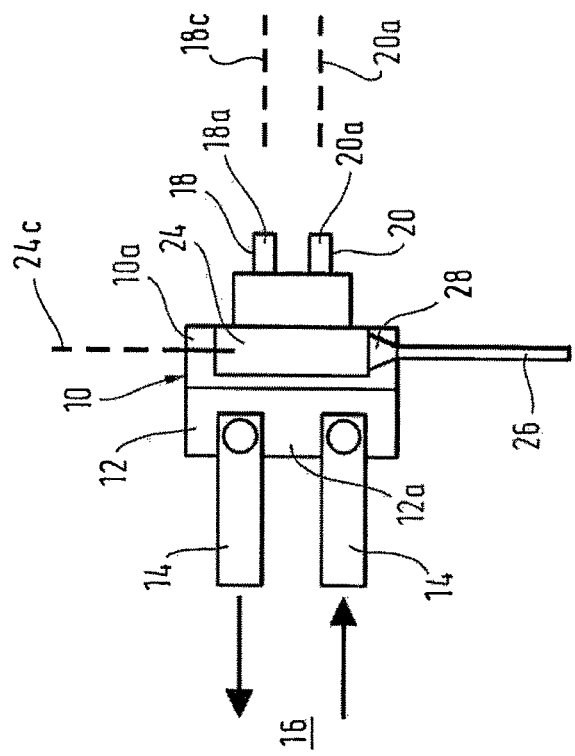
FIG. 1 shows schematically a device for connection with the airways of a patient on ventilatory support.

In the embodiment illustrated in the figures, the invention is implemented such that the contact component 10 is a nasal prong having two tubes. The contact component 10 in the form of a nasal prong may be supported, e.g. held, by a contact component holder 12.

The contact component 10 comprises an internal lumen 10a, and the holder 12, if present, comprises an internal lumen 12a. In embodiments without a holder 12, both internal lumens 10a and 12a are positioned within the contact component 10 (see FIG. 1). The lumens 10a and 12a are in fluid connection. The contact component 10 may be detachably connected to the holder 12 (if present) by a push-fit fitting or plug-in connector, which also accommodates a fluid connection line between the lumen 10a in the contact component 10 and the lumen 12a in the holder 12 (if present).

Figure 8:
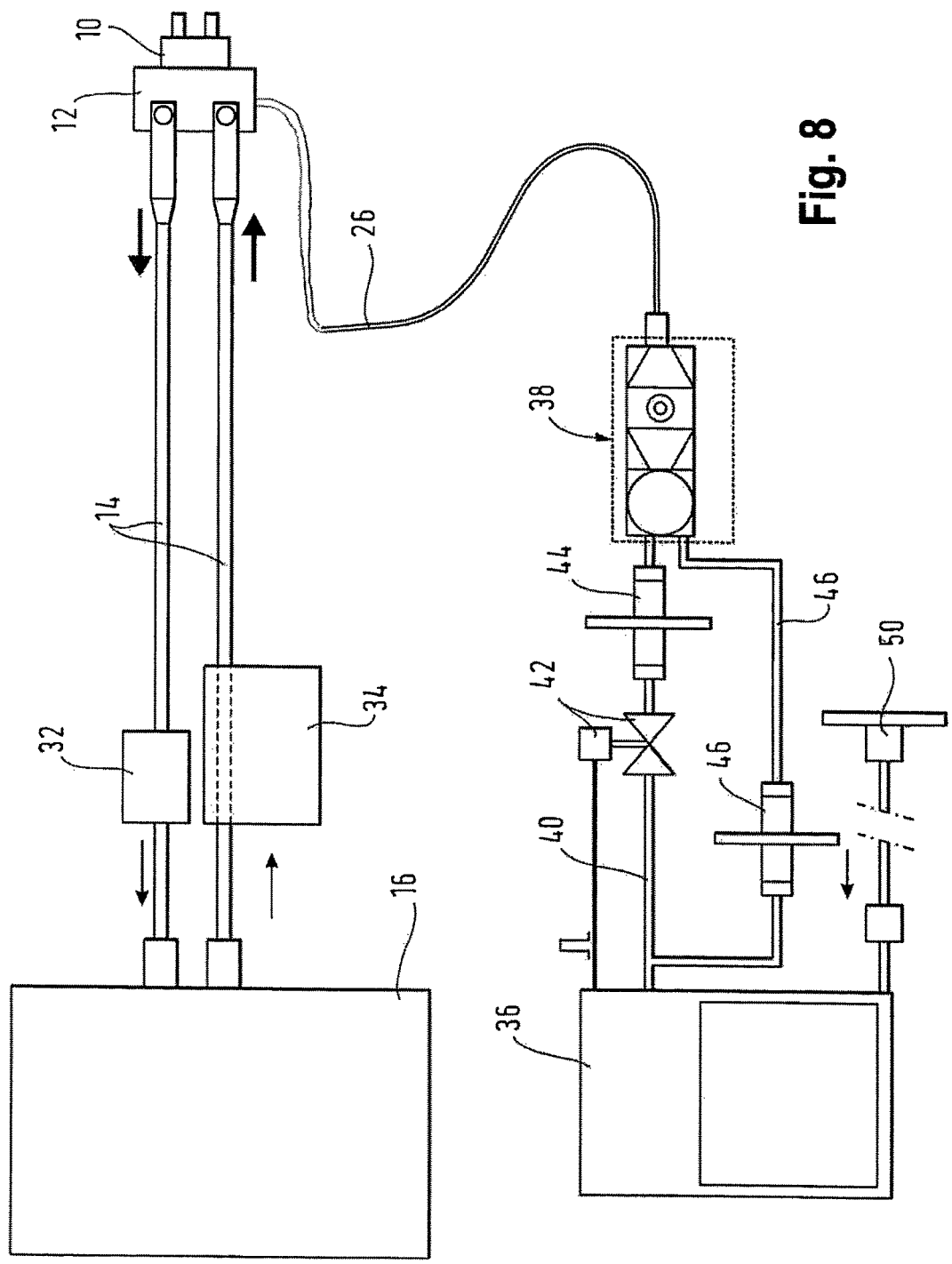
FIG. 8 shows a schematic diagram of a system for administration of an aerosol to a patient on ventilatory support.

Tubing 14 allows gas circulation between the lumen 12a in holder 12 (or in the contact component if no holder is present) and a ventilatory device such as, e.g., a CPAP machine 16, see FIG. 8.

Figure 2:
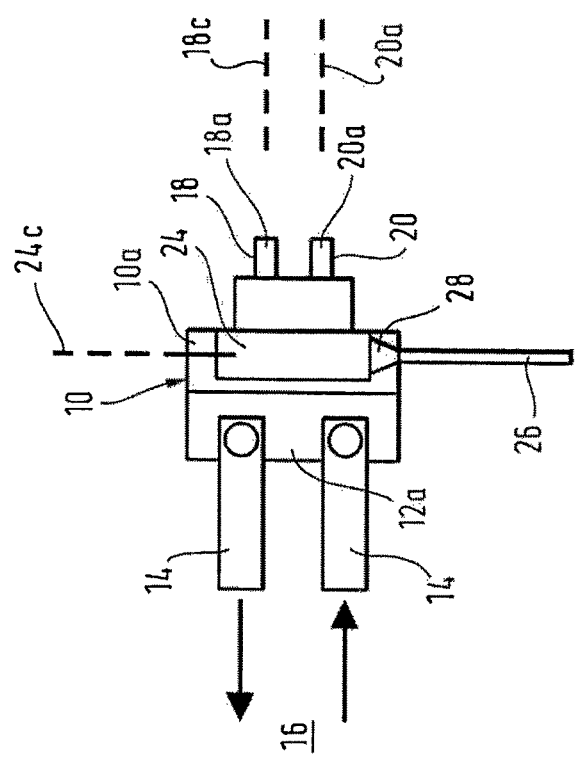
FIG. 2 shows a variant of a device according to FIG. 1 comprising a contact component holder.
Figure 3:
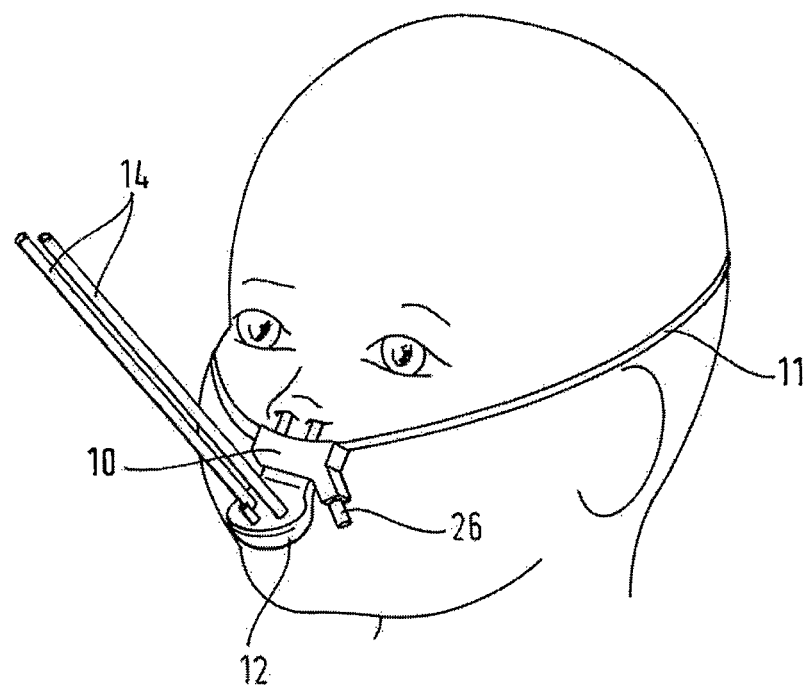
FIG. 3 shows a device according to one of the FIGS. 1 and 2 in operative position connected to an infant to be provided with ventilatory support, to whom an aerosol is to be administered.
Figure 7:
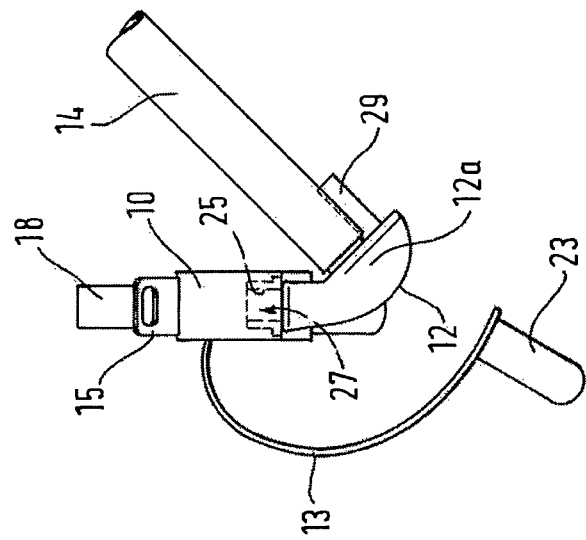
FIG. 7 shows a side view of the device according to FIG. 6.
Figure 6:
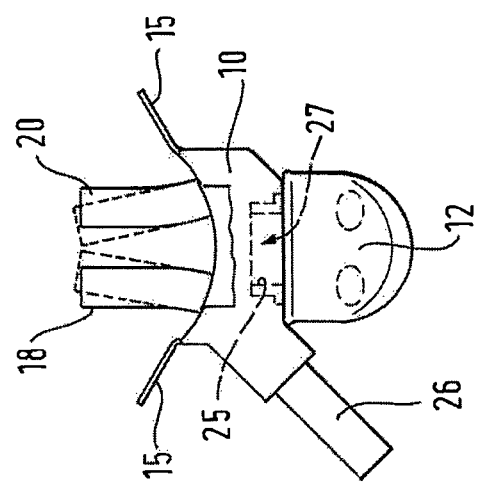
FIG. 6 shows the device according to FIG. 5 in a connected state.
Figure 5:
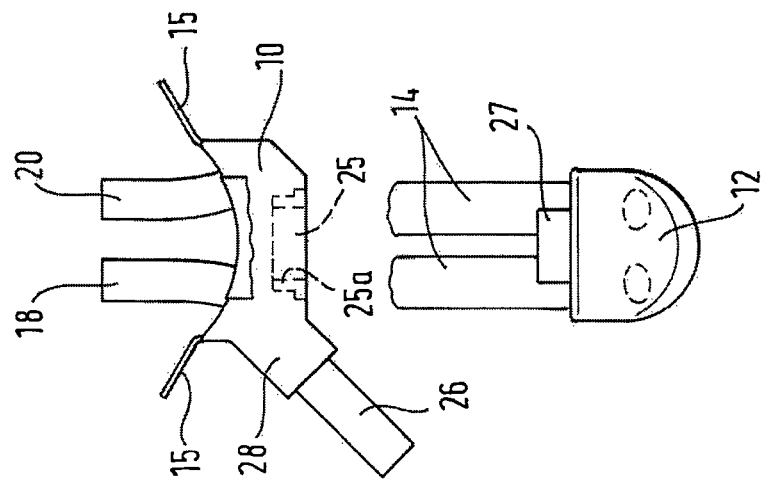
FIG. 5 shows the device for connection with a patient's airways composed of a contact component and a holder, shown in a separated state.

The contact component 10 according to FIGS. 1 and 2 comprises two tubes 18, 20 adapted to be inserted into the nostrils of a patient. Such nasal prongs having tubes are known in the art as such. Each tube 18, 20 has an inner lumen 18a and 20a (the first lumens), respectively. In the embodiment according to FIGS. 1 and 2, the first lumens 18a, 20a are in fluid connection with the second lumen 24 inside the contact component 10 which, in turn, is in fluid connection with the ventilatory device 16 through tubing 14 and the lumen 12a. One of the nasal tubes 18 and 20 may be longer than the other tube.

In the embodiment illustrated in FIGS. 1 and 2, aerosol is injected through tube 26 and port 28 into the second lumen 24 in the contact component 10. The generation of the aerosol is described in association with FIG. 8. Second lumen 24 serves as a mixing chamber (or "stratification chamber") to mix the aerosol with breathing gas, containing oxygen, introduced from the ventilatory device 16 through tubing 14 and lumen 12*a* inside the holder 12 or inside the contact component 10 into the second lumen 24 in the contact component 10.

The arrangement of the flow direction of aerosol relative to the longitudinal axes 18*c*, 20*c* of the nasal tubes 18 and 20, respectively, and relative to the longitudinal axis 24*c* of the lumen 24, is described hereinafter.

The longitudinal axis 24*c* and the longitudinal axes 18*c* and 20*c* of the tubes 18 and 20, respectively, are shown in FIG. 1. As is shown in FIGS. 1 and 2, tube 26 and port 28 are arranged such that the aerosol flow direction is essentially in line with the longitudinal axis 24*c* of the lumen 24. This may be called "tangential" flow. The advantages of this flow direction, which is substantially perpendicular to the axes 18*c* and 20*c*, respectively, are outlined above.

Alternatively, the breathing gas flow may be directed into the lumen 24 at an acute angle with respect to the nasal tubes 18, 20. In a still further alternative, the breathing gas flow may be directed into the lumen 24 in a direction substantially perpendicular to the longitudinal axis of the tubes 18, 20. In such a case, the direction of the breathing gas flow may also be substantially perpendicular to the flow direction of the aerosol gas flow within the lumen 24.

FIG. 3 shows a device according to FIG. 1 or 2 in operative state, i.e. mounted for providing ventilatory support to an infant. A strap 11 secures the device to the infant's head. The other elements shown in FIG. 3 are already described above. In the present specification, the same reference numerals are used for identical or similar components so that repeated description is not necessary.

FIG. 4 shows the device illustrated only schematically in FIG. 2 in more detail and perspective views. In addition to the components already described above in connection with FIG. 2, the contact component 10 is equipped with a strap 13 which can be used to securely connect the contact component 10 and the holder 12. To this end, the strap 13 is wrapped around the holder, and a dome 23 is used to secure the strap 13 at a socket 29 of the holder 12, see also FIG. 7.

The contact component 10 is also equipped with two mounting links 15 to be attached to the above described strap 11 shown in FIG. 3.

The strip 13 may also be secured at the holder 12 by means of a hole 17 in the strap 13 that fits onto a protrusion 17*a* of the holder 12.

FIG. 5 shows the contact component 10 and the holder 12 in a separated state. For connecting the contact component 10 to the holder 12, the holder 12 comprises a socket 27 which fits in an air-tight manner into an opening 25 formed in the contact component 10. Contact component 10 is preferably made from a relatively soft silicone material. To secure the connection between the holder 12 and the contact component 10, the hole 25 is reinforced by a lining 25*a*.

FIG. 6 shows the contact component 10 and the holder 12 in a connected (mounted) condition, i.e. with the socket 27 inserted into the hole 25 in an air-tight manner. In this connected state, in the embodiment shown in FIG. 2, the lumen 12*a* in the holder 12 is in fluid connection with the lumen 24 in the contact element 10, because the lumen 12*a* may be formed at least in part in the socket 27. Further, the lumen 10*a* of the contact component 10 may be formed at least in part in the opening 25. Therefore, when the socket 27 is fitted into the opening 25, the lumens 10*a*, 12*a* are in fluid communication. Further, because the lumen 10*a* is in fluid communication with the lumen 24, the holder 12, when fitted to the contact component 10, is also in fluid communication with the lumen 24. FIG. 6 also indicates that the tubes may be, and preferably are, manufactured from a flexible material (e.g., silicone), which allows them to easily adapt their shape and orientation to the individual anatomy of a given patient.

FIG. 7 illustrates the arrangement of the components shown in FIG. 6 from the side, i.e. rotated by 90°. In this perspective, the strap 13 is illustrated which, at one end, is connected to the contact component 10 while the other end of said strap 13 comprises a dome 23 which can be pushed onto the socket 29 of the holder 12 in order to secure the contact component 10 in an air-tight manner to the holder 12.

FIG. 8 shows schematically a system for providing ventilatory support to a patient. That system utilizes a contact component and contact component holder 12 according to one of the variants described above.

A ventilatory device 16 generates a flow of breathing gas, containing a normal or an increased fraction of oxygen, at a typical positive pressure of e.g. 5 to 8 mbar. Said breathing gas passes through a humidifier 34 and enters the contact component 10 through the holder 12.

In the embodiment shown in FIGS. 1 and 2, the breathing gas circulates through the lumen 24 in the contact component 10 and is mixed with aerosol as described above.

As is shown in FIG. 8, the system comprises a control unit 36 and a disperser 38, i.e. a means to generate an aerosol from a powdery pharmaceutical preparation. For example, the pharmaceutical preparation may be lung surfactant. In a preferred embodiment, the disperser generates a continuous flow of aerosol, which may be homogeneous or pulsed. Typically, pressurized air is delivered via the control unit 36 through line 40 and a valve 42 in pulsed form to the surfactant disperser 38. A filter 44 may be incorporated into line 40.

A disperser that is particularly well suited to be used together with the present invention is known from WO2006/108558.

Also an auxiliary airline 46 may be included with a filter 48, the auxiliary air making sure that sufficient flow of aerosol towards the contact component takes place.

Pressurized air is typically obtained through a hospital air supply 50, or may be provided by a source of compressed air (i.e., a compressed gas cylinder).

The aerosol generated by the disperser 38 is transferred through the tube 26 to the contact component 10 as described above.

To avoid contamination of the ventilatory device 16 by aerosol, a filter unit 32 can be integrated into the tubing 14.

A ventilatory device 16 generates a flow of breathing gas containing oxygen at a typical positive pressure of e.g. 5 to 6 mbar. Said breathing gas passes through a humidifier 34 and enters the contact component 10 through the holder 12.

The invention claimed is:

1. A device for connection of the airways of a child, infant, neonate or pre-term neonate patient on ventilatory support with a source of a breathing gas and a source of an aerosolized powder, said device comprising
a contact component adapted to be positioned in contact with the airways, the contact component comprising:
two first tubes each comprising a first lumen or lumens through which breathing gas and aerosolized powder can be delivered to the airways of the patient;
a second lumen which is in fluid connection with the first lumen or lumens of the two first tubes and having a longitudinal axis extending substantially perpendicularly to longitudinal axis or axes of the first lumen or lumens;
and
a second tube leading from the source of the aerosolized powder to a first port connected to the second lumen in the contact component through which the aerosolized powder can be introduced into said second lumen, and arranged such that the aerosolized powder and the breathing gas can be mixed in the second lumen;
the device being characterized by a third lumen being connected to a device for generating a flow of breathing gas, wherein the second lumen is positioned proximal to, and is in fluid connection with, said third lumen, through a second port wherein the first port is configured to introduce the aerosol into said second lumen essentially perpendicular to the longitudinal axis of the two first tubes or one of the two first tubes into said second lumen, and wherein the second port is configured to introduce the breathing gas into said second lumen essentially parallel to said longitudinal axis of the two first tubes or one of the two first tubes into said second lumen.

2. The device according to claim 1, characterized in that the contact component is removably connected to a contact component holder which comprises the third lumen.

3. The device according to claim 2, characterized in that the contact component comprises an inlet lumen adapted to receive a contact component holder lumen, wherein the inlet lumen is in fluid connection with the second lumen.

4. The device according to claim 1, characterized in that the contact component is a nasal prong.

5. The device according to claim 1, characterized in that the two first tubes are designed to be inserted into the patient's nostril or both nostrils, or the patient's nasal cavity.

6. The device according to claim 1, characterized in that the connection of the third lumen to the device for generating a flow of breathing gas is via at least one third tube.

7. The device according to claim 1, characterized in that the first port is configured to direct the aerosolized powder into said second lumen coaxially with or at an acute angle with respect to a longitudinal axis of the second lumen.

8. A combination of the contact component according to claim 1, a contact component holder and optionally a means to secure the contact component to the contact component holder, characterized in that: the contact component comprises a lumen, the contact component holder comprises a lumen, and when the contact component holder holds the contact component, the lumens of the contact component and the contact component holder, respectively, are in fluid connection.

9. A system for administration of an aerosolized powder to a child, infant, neonate or pre-term neonate patient on ventilatory support, the system comprising a device for connection with the patient's airways according to claim 1, a device for generating a flow of breathing gas, means for generating said aerosolized powder, wherein flows of breathing gas and aerosolized powder are introduced into said contact component.

10. The system according to claim 9, comprising a holder and characterized in that said holder and said contact component are detachably connectable.

11. The system according to claim 10, characterized in that the holder comprises a lumen in fluid connection with the second lumen of the contact component.

12. The system according to claim 10, characterized in that the contact component comprises a flexible strap which is detachably connectable at said holder.

13. The system according to claim 9, characterized in that the tubes can be inserted into the patient's nostril or both nostrils, or the patient's nasal cavity.

* * * * *